United States Patent
Levitsky et al.

[11] Patent Number: 5,857,461
[45] Date of Patent: Jan. 12, 1999

[54] MULTIPLE CHANNEL SAMPLE PORT

[75] Inventors: Gershon Levitsky; Joshua L. Colman, both of Jerusalem, Israel

[73] Assignee: Oridion Medical Ltd., Jerusalem, Israel

[21] Appl. No.: 912,776

[22] Filed: Aug. 18, 1997

[30] Foreign Application Priority Data

Aug. 26, 1996 [IL] Israel ........................................ 119131

[51] Int. Cl.⁶ .................................................. A61M 16/00
[52] U.S. Cl. ............................... 128/207.14; 128/205.23; 128/204.16
[58] Field of Search .................. 128/207.14, 205.23, 128/200.21, 200.24, 204.16, 203.12; 60/532, 529

[56] References Cited

U.S. PATENT DOCUMENTS

| | | | |
|---|---|---|---|
| 4,558,708 | 12/1985 | Labuda et al. | 128/719 |
| 5,333,607 | 8/1994 | Kee et al. | 128/204.18 |
| 5,711,294 | 1/1998 | Kee et al. | 128/202.27 |
| 5,789,660 | 8/1998 | Kofoed et al. | 73/23.2 |

*Primary Examiner*—John G. Weiss
*Assistant Examiner*—Charles W. Anderson
*Attorney, Agent, or Firm*—Mark M. Friedman

[57] ABSTRACT

A multiple channel sample port for an airway adaptor, which includes a substantially spherical projection with a plurality of inlet tubes and an outlet, which is designed to be placed substantially within the main channel of the airway adaptor through an opening in the side wall of main channel of the airway adaptor. The outlet is connected to, or integrally formed with, one end of a substantially cylindrical chamber. The opposite end of the substantially cylindrical chamber is adapted to be connected to a gas analyzer. When a pressure reduced below atmospheric pressure is applied at the gas analyzer, gas flows from the main channel of the airway adaptor into the inlets of the substantially spherical projection, through the spherical projection into the substantially cylindrical projection, and from thence to the gas analyzer.

21 Claims, 5 Drawing Sheets

MULTIPLE CHANNEL SAMPLE PORT

FIELD AND BACKGROUND OF THE INVENTION

The present invention relates to an airway adaptor with a sample port, and, more particularly, to an airway adaptor with a sample port which includes an air collector with multiple inlets.

For purposes of description, the discussion herein is focused on airway adaptors for use with human patients, it being understood that the present invention is not limited in scope only to use with patients and can beneficially be used in various other contexts.

Airway adaptors are generally used to collect gas samples for analysis, particularly from the exhaled breath of hospitalized patients who require a breathing apparatus, such as patients under anesthesia or those patients on life support systems. Typically, an endotracheal tube extends from such a patient to a breathing apparatus, carrying gases to the patient and the exhaled breath of the patient away from the patient. The adaptor connects the section of the endotracheal tube leading from the patient to the section leading to the breathing apparatus. The adaptor may be in the shape of a "T", such that these adaptors are also known as "T-pieces". The top or cross-piece of the "T" is a tube, through which gases travel to the patient, and through which the exhaled breath returns from the patient. The other part of the "T" is a port which projects from the wall of the tube, and is used to collect samples of the gas flowing through the tube. Alternatively, the adaptor may be in the shape of an elbow, such that this type of adaptor is also called an "elbow piece". The tube in these adaptors forms the elbow, and the port again projects from the wall of the tube.

In either type of adaptor, the port is connected at its other end to a gas analyzer. A sidestream of the patient's exhaled breath flows through the port, to the gas analyzer to be analyzed. The results of this non-invasive analysis provide an indication of the patient's condition, such as the state of the patient's pulmonary perfusion, respiratory system and metabolism.

The accuracy of this non-invasive analysis of exhaled gases depends on the ability of a sampling system to move a gas sample from the patient to the gas analyzer while maintaining a smooth, laminar flow of gases, such that there are as few alterations to the waveform and response time of the gases as possible. The waveform of the gas is critical for accurate analysis. As gas travels from the patient to the gas analyzer, it moves in a wave. The composition of gases changes throughout this wave, defining the waveform. These changes can occur within 10–100 msec, and give important information about the condition of the patient. Internal mixing of the gas sample, or alterations in the waveform, reduces the accuracy of the analysis of the sample by the gas analyzer, and reduces the amount of information obtained from that analysis.

Internal mixing of the gas sample and alterations in the waveform both slow the response time. As each gas travels in a wave, the wave has peaks, or high concentrations of gas. The response time is the time elapsed between the appearance of the base of a peak and the appearance of the peak itself. A fast response time indicates that the peaks are relatively tall and narrow, and that the peaks have not broadened since the gas was exhaled from the patient. Since the accuracy of the gas analysis, and the information obtained from that analysis, depend upon the waveform remaining substantially unaltered, a fast response time is desirable.

Merely stabilizing one of these factors is not sufficient for the accurate analysis of a gas sample. Alterations in one of these factors tend to affect the other factors, multiplying the changes to the gas sample, and exponentially reducing both the accuracy of the gas analysis, and the amount of information obtained from that analysis. For example, mixing of the gas tends to slow the response time. Thus, it is crucial that the airway adaptor alters these factors as little as possible.

A significant obstacle to preventing these alterations to the gases, and hence to obtaining an accurate gas analysis, is that the exhaled breath of such patients frequently contains substances which can block or clog the sampling apparatus, such as liquid or solid secretions, or mixtures thereof, including mucous, saliva and condensed water. Therefore, the airway adaptor must include means for separating the desired exhaled gases from these solids, liquids, or mixtures thereof. These separating means are placed in either the tube or the port of the airway adaptor. However, such means are also subject to blocking or clogging, which can reduce the pressure of gases traveling through the airway adaptor to the gas analyzer. Such a pressure drop may cause numerous alterations to the gas sample, including alteration of the waveform, mixing of the gas, and alterations in gas concentration, all of which reduce the accuracy of the gas analysis, and the amount of information obtained from that analysis. The concentration of the gas is particularly affected by changes in pressure, since gas concentration is directly dependent on the pressure of the gas, and is usually presented in units of millimeters of mercury. Hereinafter the term "pressure drop" refers to a decrease in the pressure exerted by the gas itself.

The need for an accurate analysis of the gas, as well as the overall demands of human gas analysis, dictate the required features of an airway adaptor. First, the gases should be separated from the liquids, solids or mixtures thereof, while maintaining a smooth, laminar flow of gases, and without a production of substantial pressure drops, or an alteration in the gas waveform. Second, minimal added void volume should be present in the adaptor or sample port, which might cause mixing of gases. These characteristics are critical for accurate sample analysis and for obtaining maximum information from the analysis, since mixing of gases, disruption of the smooth, laminar flow of gases, or alterations in the waveform of the gases can produce significantly inaccurate results, as described above. Furthermore, pressure drops tend to exacerbate gas mixing, reductions in gas flow rate, and alterations of gas waveform, and should therefore be avoided.

Further features are dictated by the demands of human gas analysis. The airway adaptor employing a means of separation should be low maintenance; that is, it should not require frequent cleaning or replacement. Also, the airway adaptor should be easy to use. Unfortunately, currently available adaptors have serious flaws. These less viable adaptors can be easily distinguished from the present invention, which successfully meets the requirements.

These previously known adaptors have often included a filter in the sample port for separating gases from liquids, solids and combinations thereof. Other such adaptors have filters or baffles in the tube of the airway adaptor. However, none of these filter-based constructions solves the inherent tendency of hydrophobic, porous materials to substantially increase the pressure drop of the gas as it crosses the filter, interfering with the waveform and reducing the accuracy of the sample analysis. Furthermore, such a pressure drop tends to increase over time, as patient secretions and condensed water collect on or in the filter. For example, a simple flat filter with a relatively small surface area, such as that disclosed in U.S. Pat. No. 4,456,014 to Buck et al., is easily covered with patient secretions or condensed water, which accelerates this drop in pressure.

Increasing the diameter of the filter so that it is larger than the sample port diameter, such as in U.S. Pat. No. 4,679,573 to Parnoff et al. (hereinafter referred to as "Parnoff"), reduces the rate at which such a filter may become blocked. However, in order to avoid adding void volume to the sampling apparatus, the design of the Parnoff airway adaptor has the filter lying against the tube wall, which increases the tendency of the filter to become covered with condensed water or patient secretions.

The surface area of the filter can be increased without increasing the diameter, if the shape of the filter is altered from flat to dome-like or conical, as described in both Parnoff and PCT Application No. US 90/04353 to Wo. However, the dome must have thick walls in order to maintain its shape under pressure, which encourages the mixing of gases, since the flow rate is sharply reduced by the thickness of the walls. Furthermore, the thickness of the walls adds void volume to the sample apparatus. Finally, the filter membrane must have a small pore size to prevent the entry of condensed water and other liquids, which further interferes with the smooth, laminar flow of gases, and increases the pressure drop.

A filter or baffle can be added to the tube of the airway adaptor itself, rather than to the sample port, which may reduce added void volume. For example, an inner lining of the airway adaptor itself can be made permeable only to gas, so that gas escapes to the sample tube, while liquids and solids are trapped in the adaptor. In this sense, the tube itself is the filter, as described in U.S. Pat. No. 4,985,055 to Thorne et al. Alternatively, a baffle may be placed in the tube of the adaptor, rather than a filter, as described in U.S. Pat. No. 4,558,708 to Labuda et al. However, condensed water which collects on the walls of the tube of the airway adaptor quickly fills this type of baffle, after which the baffle is no longer effective. Filled baffles are heavy, and tend to put a strain on the connections between the airway adaptor and the endotracheal tubing. These baffles also introduce further amounts of void volume. Furthermore, neither configuration solves the inherent tendency of filters and baffles to become blocked. Indeed, these adaptors may themselves become blocked by liquid or solid material, with a potentially adverse effect on the patient.

Alternatively, a backflush device can be used to remove liquid or solid material which is blocking the filter, as in U.S. Pat. No. 5.042,522 to Corenman et al. However, such a device still does not solve the problem of the decrease in gas pressure as the gas crosses the filter, nor the related problem of slow response times.

Clearly, filters are not an adequate solution due to the inherent flaws in their performance. It is known in the literature to construct an adaptor which does not rely on filters for separating gases from liquids, solids or mixtures thereof. E.P.C. No. 0275105 to Spacelabs, Inc. (hereinafter referred to as "Spacelabs") describes an adaptor which does not use any kind of filter or filter-like device. The tube of the adaptor of Spacelabs has two chambers, connected by radial channels extending from the inner chamber to a chamber which is in the form of an annular channel. This annular channel is formed in a section of the adaptor with a constricted diameter. The gases flow from the inner chamber through the radial channels to the annular channel, and from the annular channel to the port.

The adaptor of Spacelabs is not an adequate solution to the problems above. Airflow through the airway adaptor may be compromised, since the diameter of the adaptor is constricted. Furthermore, the port of the adaptor of Spacelabs will tend to suck in water or other liquids if the port is not kept upright. Keeping the port upright is unrealistic in a hospital environment, since the adaptor may be incorrectly installed by hospital staff, and since patients may move, which can cause the tube and the port to rotate, requiring frequent repositioning of the adaptor.

The present invention also does not rely upon a filter to separate gases from liquids, solids or mixtures thereof. Thus, the present invention is not subject to the inherent flaws of adaptors which rely upon filters. Furthermore, the present invention can be easily distinguished from, and is greatly superior to, the adaptor of Spacelabs, since the present invention alters the structure of the port of the airway adaptor, rather than of the entire adaptor. The internal structure of the adaptor of the present invention is completely different from that of the adaptor of Spacelabs, and does not compromise airflow through the adaptor, nor does the port of the present invention need to be kept upright for optimum efficacy. Thus, the present invention is easier to install and to maintain, particularly since the airway adaptor of the present invention can be freely rotated in a variety of orientations, and still maintain its efficiency.

Thus, none of the above previously known configurations successfully fulfills the criteria for an airway adaptor listed above. The present invention does fulfill these criteria successfully, in a form which is clearly and easily distinguishable from the above previously known configurations.

There is thus a widely recognized need for, and it would be highly advantageous to have, an airway adaptor which does not reduce gas pressure or flow rate, or alter the gas waveform, which does not easily become blocked or clogged, which has minimal added void volume, yet which is easy to use and does not require frequent repositioning or maintenance, and which is freely rotatable, so that it is efficient in a variety of orientations.

SUMMARY OF THE INVENTION

According to the present invention there is provided an airway adaptor, comprising: (a) a tube, the tube featuring a wall; and (b) a port forming a junction with the tube through the wall, and the port including an outlet, an air collector and a plurality of inlets, the air collector being attached to the outlet, and the inlets being attached to the air collector, each of the inlets featuring an opening located substantially within the tube.

According to further features in preferred embodiments of the invention described below, the inlets are optionally holes, but are preferably substantially tubular. Each of the openings, and each of the inlets, preferably has a substantially similar internal diameter to each other of the openings, and to each other of the inlets, respectively. If the inlets are substantially tubular, the length of each of the inlets is preferably substantially similar to the length of each other of the inlets. Also, the internal diameter of each of the inlets is preferably similar to the internal diameter of its opening. Preferably, the inlets are formed of substantially hydrophobic material.

According to still further features in the described preferred embodiments, the internal diameter of the openings and of the inlets preferably lies in the range of from about 0.5 mm to about 1.7 mm. If the inlets are substantially tubular, the length of each inlet is preferably about 2.5 mm.

Most preferably, the internal diameter of the openings and of the inlets is about 0.8 mm.

According to yet further features in the described preferred embodiments, the air collector is preferably a hollow sphere, and is formed of substantially hydrophobic material, or alternately of substantially hydrophilic material. The air collector is preferably substantially centrally located within the tube, and the air collector is preferably substantially perpendicular to the wall of the tube. Optionally, the openings of the inlets may substantially face one end of the tube, in which case each of the inlets is symmetrically disposed relative to each other of the inlets. Preferably, an opening of at least one inlet is substantially facing one end of the tube, and an opening of at least another one of the inlets is substantially facing the other end of the tube. Also preferably, there are three inlets.

According to even further features in the described preferred embodiments, the inlets project into the air collector, such that an end of each of the inlets is substantially within the air collector, and there is a first distance between each of the ends, and a second distance between each of the openings, the first distance preferably being less than the second distance. Also, the internal diameter of the outlet is preferably greater than the internal diameter of each opening.

Also according to the present invention, there is provided a method of using the present invention for withdrawing a sidestream, comprising: (a) attaching the airway adaptor to a conduit for conducting gas; (b) connecting the outlet of the port to a gas analyzer; and (c) applying a force at the gas analyzer, such that gas flowing through the airway adaptor moves from the airway adaptor to the gas analyzer.

According to yet another embodiment of the present invention, there is provided a method of using the present invention for administering medicine, comprising: (a) connecting the airway adaptor to a breathing apparatus of a patient; and (b) placing the medicine in said port of the airway adaptor.

Also according to the present invention, there is provided a sample port, including: (a) an outlet; (b) an air collector, the air collector being attached to the outlet; and (c) a plurality of inlets, the inlets being attached to the air collector, and each of the inlets featuring an opening, the opening being located substantially within the tube.

The present invention successfully addresses the shortcomings of the presently known configurations by providing an airway adaptor which permits accurate analysis of gas samples, without significantly reducing the pressure or the flow rate of sampled gas, without mixing of the gas waveform, with low rates of blocking, clogging, required maintenance, repositioning or replacement, yet which is easy to use.

More specifically, the present invention is an air adaptor, with a port and a tube. The port forms a junction through the wall of the tube, and provides access to the interior of the tube. The port includes an outlet, an air collector, and a plurality of inlets. The air collector is attached to the outlet, and the inlets are attached to the air collector. One end of each of the inlets is located substantially within the tube. Hereinafter, the term "attached" is defined as connected to, or integrally formed with.

The port is preferably substantially perpendicular to the wall of the tube of the airway adaptor, and the air collector preferably sits substantially in the center of the tube of the adaptor, substantially perpendicular to the wall of the tube, such that the inlets do not contact the inner wall of the tube.

The present invention is intended to be used in the following manner. A sidestream or sample of gas flows from the tube of the air adaptor, through the inlets of the air collector, and thence through the outlet of the port. In a preferred method, the gas then flows to a gas analyzer. Preferably, a force is applied at the gas analyzer, to cause a sidestream of gas to flow from the tube of the air adaptor to the gas analyzer.

The invention is designed to resist blockage by, or intake of, mucous, saliva, other solids, liquids or mixtures thereof. These solids, liquids or mixtures thereof, are unable to enter the inlets of the air collector unless all of the inlets are blocked. If all the inlets are not blocked, there is not sufficient external pressure to overcome the resistance of the inlets to intake of solids, liquids, or mixtures thereof, because of the small internal diameter of the inlets and the hydrophobicity of the material from which they are formed. The inlets are placed so that a single solid particle or liquid drop would be unable to block all inlets simultaneously.

The term "hydrophobic" is used herein to refer to substances which resist contact with liquids, or other materials which contain water. The term "hydrophilic" is used hereinafter to refer to substances which encourage contact by liquids, or other materials which contain water.

A second method of use for the present invention is the administration of medicines in a nebulized, or otherwise airborne, pharmaceutical preparation to the patient via the port of the airway adaptor of the present invention. In this method, such medicines are placed within the port of the airway adaptor. When the patient inhales, the medicine is pulled from the port, through the air collector and into the tube of the airway adaptor. From the tube of the airway adaptor, the medicine is pulled into the endotracheal tube of the patient, and from thence into the patient's lungs.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an air adaptor which can effectively be used to collect samples of gas without reducing the pressure or the flow rate of the collected gas, and which is substantially less sensitive to its orientation, and less likely to become blocked by, or to intake, liquid or solid material, or their mixtures thereof, such as mucous or saliva. Specifically, the present invention has a tube and a port, which forms a junction through a wall of the tube, and which provides access to the interior of the tube. The port includes an outlet, an air collector, and a plurality of inlets. The air collector is attached to the outlet, and the inlets are attached to the air collector. One end of each inlet is substantially located within the tube.

The principles and operation of an airway adaptor according to the present invention may be better understood with reference to the drawings and the accompanying description.

Figure 1A:
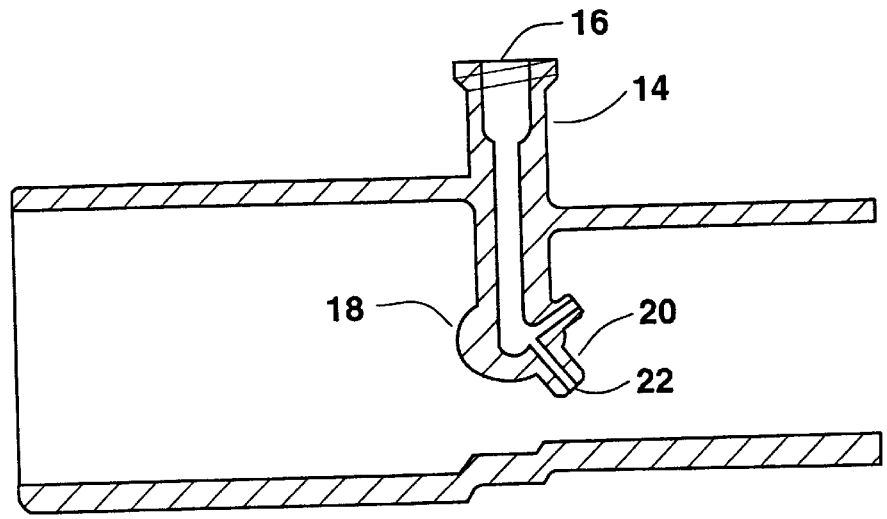
FIGS. 1A and 1B are a schematic view of an illustrative airway adaptor according to the present invention, with a substantially spherical air collector and with substantially tubular inlets.
Figure 1B:
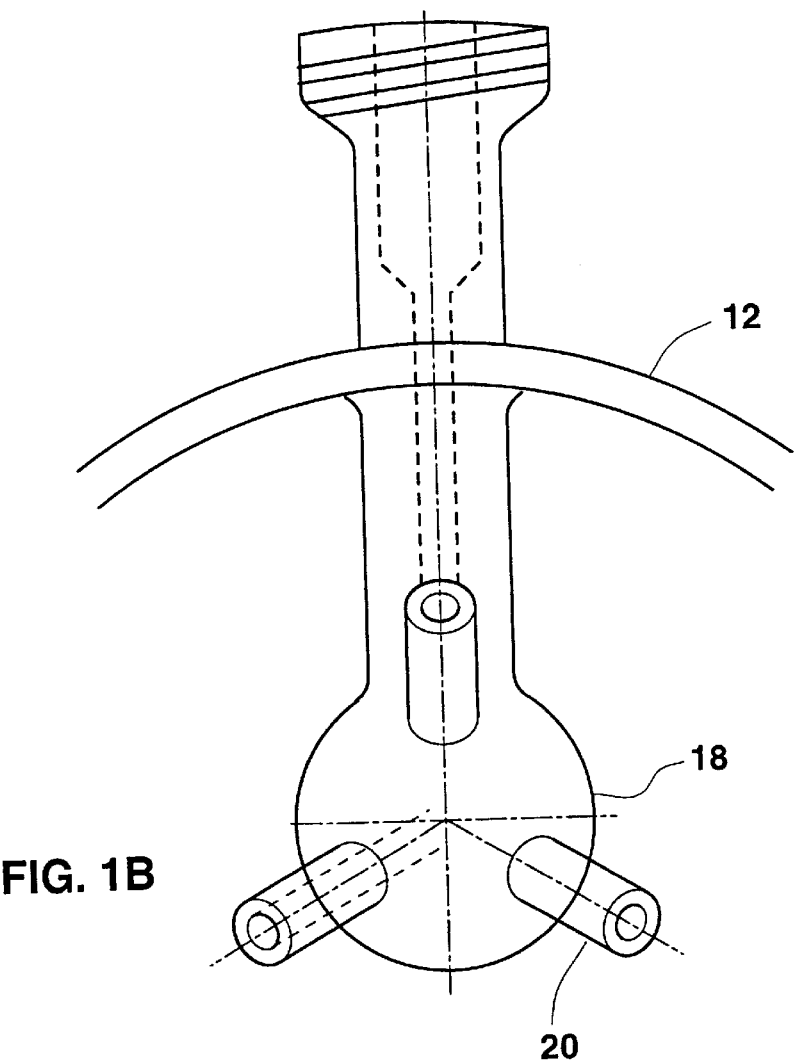

Referring now to the drawings, FIGS. 1A and 1B are schematic views of an illustrative airway adaptor according to the present invention. FIG. 1A is a longitudinal cross-sectional view of an airway adaptor 10. Airway adaptor 10 has a tube 12 and a port 14. As shown in the preferred embodiment illustrated, tube 12 is substantially straight, such that air adaptor 10 may be described as a "T-piece". However, tube 12 may also be bent, in an elbow shape, such that airway adaptor 10 may be described as an "elbow piece" (see FIGS. 7 and 8). Port 14 is attached to tube 12. Port 14 forms a junction through a wall of tube 12. Port 14 has an outlet 16, an air collector 18 and a plurality of inlets 20. Air collector 18 is attached to outlet 16, and inlets 20 are attached to air collector 18. Outlet 16 may be adapted to connect to a gas analyzer (not shown). Each inlet 20 has an opening 22, which is substantially within tube 12.

FIG. 1B shows a second cross-section of the airway adaptor of FIG. 1A. Tube 12 is seen end-on. Preferably, air collector 18 is a hollow sphere, and inlets 20 are substantially tubular (see FIG. 2).

Figure 2A:
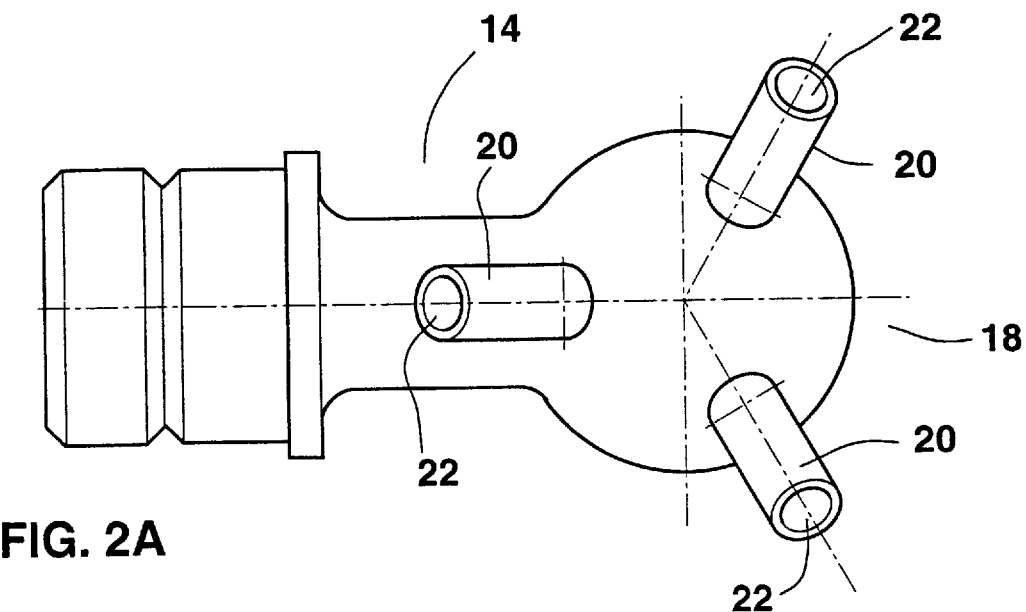
FIGS. 2A and 2B are views of the port of FIGS. 1A and 1B, according of the present invention.
Figure 2B:
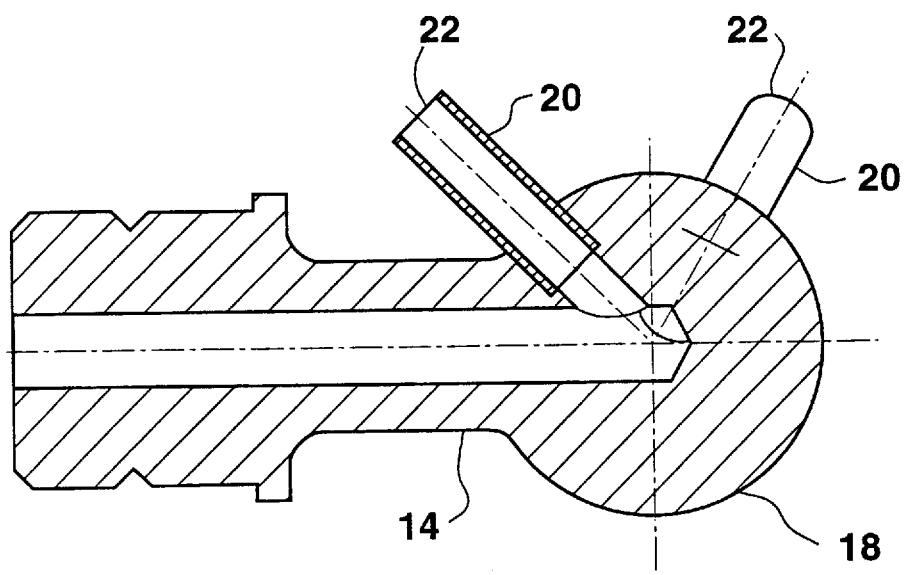

FIG. 2A is a front view of port 14 of FIG. 1 alone, without tube 12. FIG. 2B shows a longitudinal cross-sectional view of the illustrative port 14 of FIG. 2A.

Figure 3A:
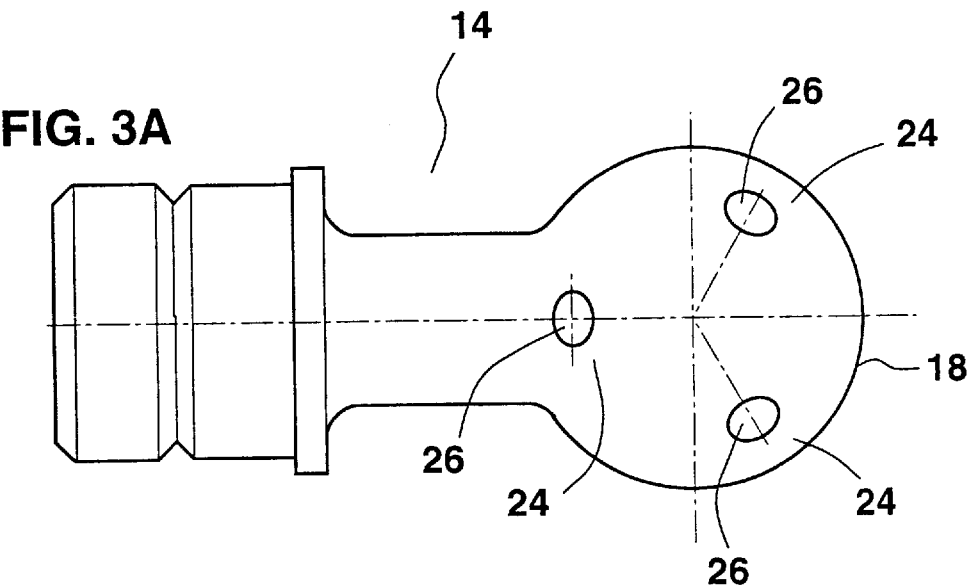
FIGS. 3A and 3B are views of another embodiment of the port of FIG. 2, with a substantially spherical air collector and with substantially flush inlets.
Figure 3B:
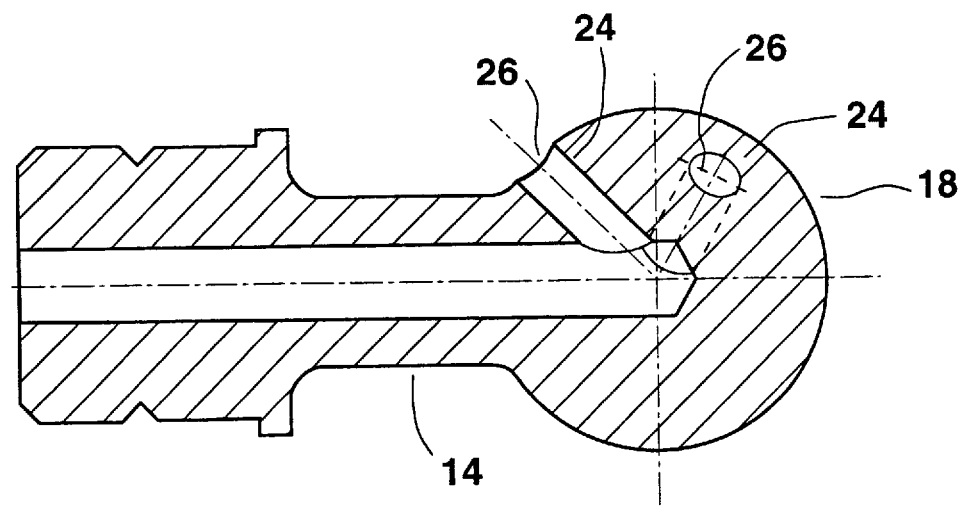

FIG. 3A shows a front view of another illustrative embodiment of port 14 of FIG. 1. FIG. 3B shows a longitudinal cross-section of port 14 as illustrated in FIG. 3A. In this embodiment, inlets 24 are substantially flush against air collector 18, and have openings 26. Inlets 24 may be co-extensive with openings 26, such that inlets 24 and openings 26 are the same physical entity, and inlets 24 are holes.

Figure 4:
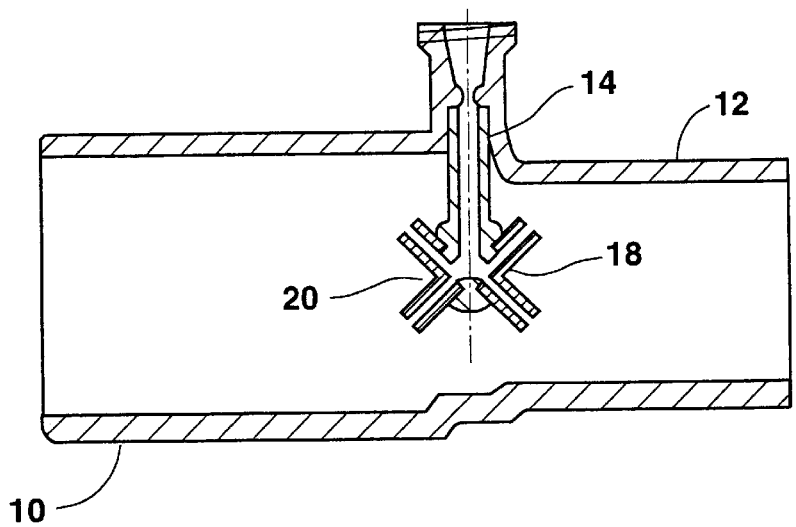
FIG. 4 is a view of an embodiment of an illustrative airway adaptor according to the present invention, with a substantially spherical air collector and four substantially tubular inlets.

FIG. 4 shows a different embodiment of airway adaptor 10, with a substantially spherical air collector 18 and four substantially tubular inlets 20. Port 14 is a separate part, which may be placed within tube 12, rather than being integrally formed with tube 12.

Figure 5:
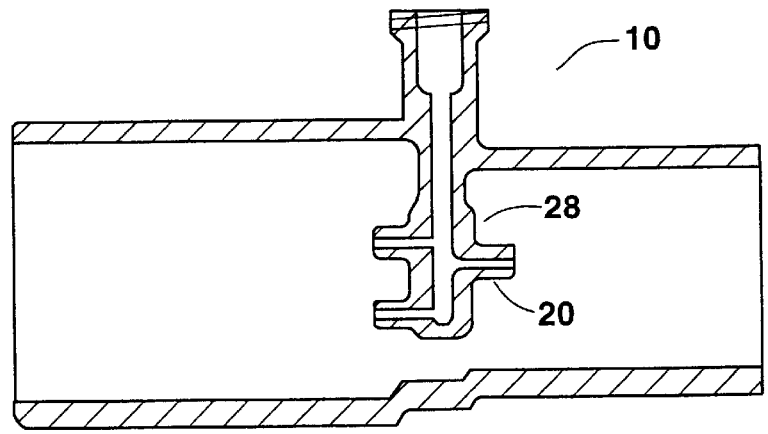
FIG. 5 is a view of yet another embodiment of an illustrative airway adaptor according to the present invention, with a substantially oval-shaped air collector and three substantially tubular inlets.

FIG. 5 shows another possible configuration of airway adaptor 10, with a substantially oval-shaped air collector 28 and three substantially tubular inlets 20. Oval-shaped air collector 28 is an effective alternative to substantially spherical air collector 18, particularly since the curved shape of air collector 28 gives it many of the same advantages of air collector 18.

Figure 6:
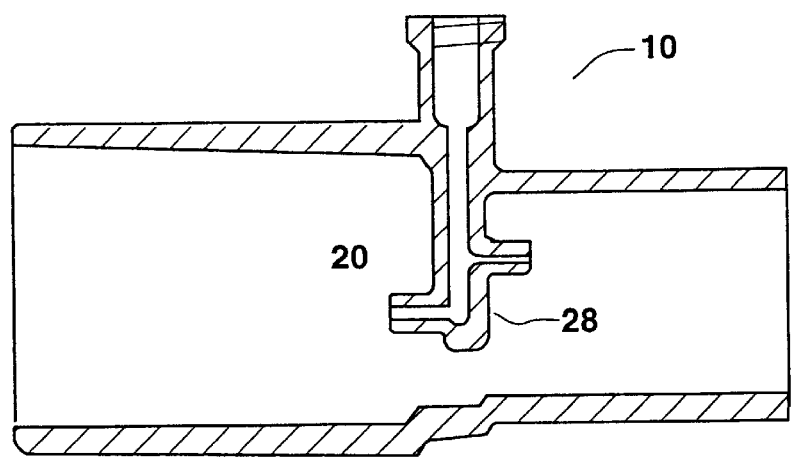
FIG. 6 is a view of still another embodiment of an illustrative airway adaptor according to the present invention, with a substantially oval-shaped air collector and two substantially tubular inlets.

FIG. 6 shows yet another possible configuration of airway adaptor 10, with air collector 28 and two substantially tubular inlets 20.

Figure 7:
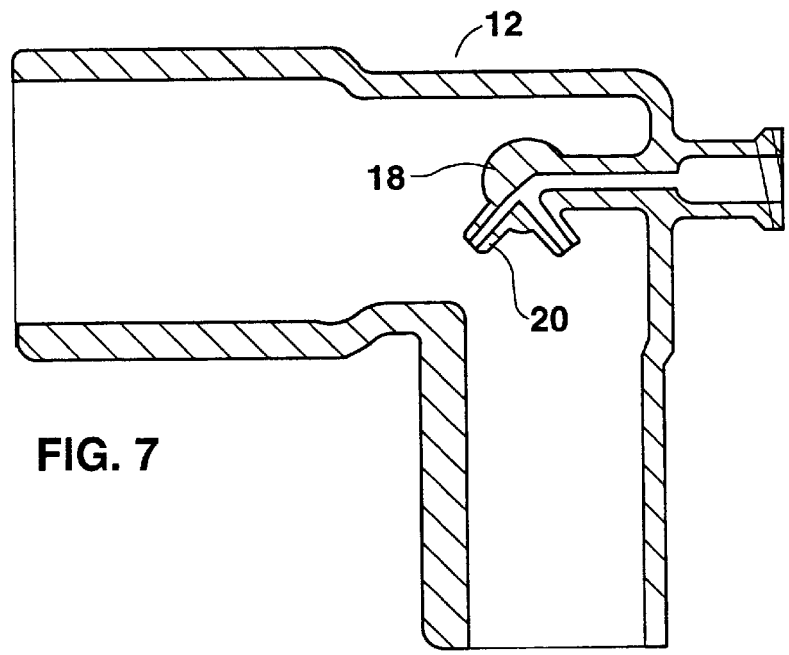
FIG. 7 is a view of an embodiment of an illustrative airway adaptor according to the present invention, with an elbow bend in the tube, a substantially spherical air collector and three substantially tubular inlets.
Figure 8:
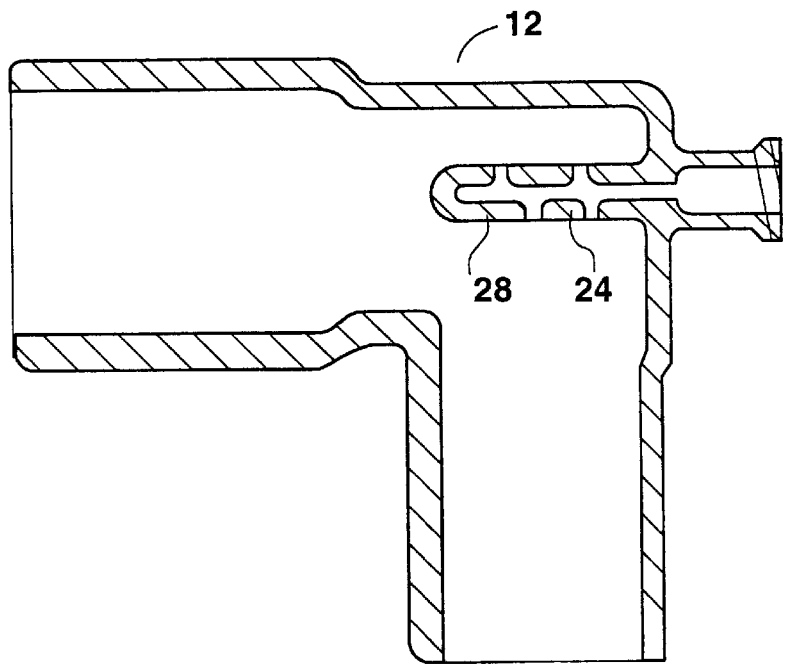
FIG. 8 is a view of an embodiment of an illustrative airway adaptor according to the present invention, with an elbow bend in the tube, a substantially oval-shaped air collector and four substantially flush inlets.

FIGS. 7 and 8 are views of airway adaptor 10 in the form of an "elbow-piece". In this configuration, tube 12 has an elbow bend. The elbow bend is particularly advantageous for breathing systems where the patient's trachea is directly intubated, as this configuration reduces stress on the trachea. FIG. 7 includes air collector 18 and three inlets 20. FIG. 8 includes air collector 28 and four inlets 24.

In all the embodiments shown, the internal diameter of outlet 16 is preferably greater than the internal diameter of inlets 20 or 24, such that internal diameter of outlet 16 is preferably larger than the internal diameter of inlets 20 or 24 by a percentage which lies in a range of from about 30% to about 50%. The greater internal diameter of outlet 16 prevents pressure fluctuations, since a plurality of inlets 20 or 24 empty into one outlet 16. If outlet 16 had a substantially similar internal diameter as inlets 20 or 24, the smooth, laminar flow of gases would be disrupted, since the total gas from all inlets 20 or 24 would enter a volume which is smaller than the total volume of all inlets 20 or 24. For similar reasons, the internal diameter of each opening 22 or 26 is preferably substantially similar to the internal diameter of each other opening 22 or 26. Also preferably, the internal diameter of each inlet 20 or 24 is substantially similar to the internal diameter of its opening 22 or 26, respectively. For inlets 20, which are substantially tubular, the length of each inlet 20 is preferably substantially similar to the length of each other inlet 20. If these dimensions were not similar, the smooth, laminar flow of gases would be disrupted.

Optionally, opening 22 or 26 of at least one inlet 20 or 24, respectively, can face one end of tube 12, and opening 22 or 26 of at least one other inlet 20 or 24, respectively, can face the other end of tube 12, as shown in FIGS. 4–6 and 8. Alternatively, openings 22 or 26 of all inlets 20 or 24, respectively, may face one end of tube 12, as shown in FIGS. 1–3 and 7. Having all openings 22 or 26 face one end of tube 12, most preferably contrary to the direction of the airflow through tube 12, has the advantage of enabling maximum airflow past port 14, but the disadvantage of potentially permitting a single droplet or particle of liquids, solids, or their mixtures thereof, to block all openings 22 or 26 at once. There are preferably three inlets 20 or 24, as shown in FIGS. 1–3, 5 and 7. In the preferred embodiment shown in FIGS. 1–3, the three inlets 20 or 24 are symmetrically placed with respect to each other, such that there is a 120 degree angle between every two inlets 20 or 24. The advantage of placing three inlets 20 or 24 symmetrically is that the distance between every pair of inlets 20 or 24 is maximized, decreasing the possibility that a single particle or droplet of solids, liquids, or their mixtures thereof, might block all three inlets 20 or 24 simultaneously.

With regard to inlets 20, which are substantially tubular, preferably, the geometry of inlets 20 and air collector 18 or 28 is such that inlets 20 project through air collector 18 or 28, and each end of an inlet 20 which is within air collector 18 or 28 has a first distance from each end of another inlet 20. Each opening 22 has a second distance from each other opening 22. Preferably, the first distance is less than the second distance. If the first distance is not less than the second distance, then two problems may occur. First, mixing of gases may occur within air collector 18 or 28. Second, a single drop of liquid, or particle of solid, or their mixtures thereof, might be able to block all of openings 22 simultaneously. Increasing the second distance minimizes the chance that this may occur.

In all embodiments shown, port 14 is preferably substantially perpendicular to tube 12, air collector 18 or 28 is preferably substantially centrally located within tube 12, and air collector 18 or 28 is preferably substantially perpendicular to the wall of tube 12. Inlets 20 should preferably not contact the inner wall of tube 12. Locating air collector 18 or 28 substantially perpendicularly to the wall of tube 12 allows inlets 20 or 24 to be maximally distant from the inner surface of the wall of tube 12. Also, locating air collector 18 or 28 substantially centrally within tube 12 exposes air collector 18 or 28 to the maximum airflow.

Specific, preferred dimensions of the components of the illustrative airway adaptor of the present invention are as follows. Air collector 18 or 28 is preferably less than about 5.5 mm in diameter (external dimension). Inlets 20, which are substantially tubular, are preferably about 2.5 mm long. The internal diameter of inlets 20 or 24 preferably lies in a range of from about 0.5 mm to about 1.7 mm, and is most preferably about 0.8 mm. These dimensions give the airway adaptor an optimum efficiency, since they allow for the most efficient collection of gases, with minimal disruptions due to intake of, or blockade by, solids, liquids, and their mixtures thereof.

In all embodiments shown, air collector 18 or 28, and inlets 20 or 24, are preferably formed from a hydrophobic material, which will resist contact with liquids, and mixtures containing liquids. Alternatively, air collector 18 or 28 may be formed from a hydrophilic material, and inlets 20 or 24 from a hydrophobic material. Inlets 20 or 24 are preferably formed from a hydrophobic material, in order to resist the entry of liquids, or their mixtures thereof, which might block or clog port 14. Air collector 18 or 28 may be formed from a hydrophilic material, which can attract liquids, or their mixtures thereof, away from inlets 20 or 24, and therefore help prevent blocking or clogging of inlets 20 or 24.

Air adaptor 10 may be used in the following manner, which describes the use of the most preferred embodiment of air adaptor 10 as illustrated in FIGS. 1 and 2, although air adaptor 10 in FIGS. 3–8 may be used in a similar manner. The example given is for sampling exhaled air from a patient connected to a breathing apparatus, and is for illustrative purposes only, since air adaptor 10 may be used to sample gases in many other ways. The endotracheal tube of the patient (not shown) is connected to tube 12 of airway adaptor 10. Outlet 16 is connected to a gas analyzer (not shown). There is provided at the gas analyzer a force, which may be in the form of a somewhat below atmospheric pressure, which encourages gas flowing through tube 12 of airway adaptor 10 to flow into air collector 18 through inlets 20. The gas then flows through outlet 16 of port 14 into the gas analyzer. Unfortunately, this force also encourages the intake of liquids, solids, or their mixtures thereof.

Liquids, solids, or their mixtures thereof, such as mucous or saliva, are discouraged from entering air collector 18 by both the size of openings 22, the placement of inlets 20, and the hydrophobic nature of inlets 20. Opening 22 is sufficiently large to admit an adequate sidestream of gas for sampling, yet is sufficiently small to encourage production of a surface tension of a fluid on opening 22, which discourages entry by liquids or mixtures containing liquids, such as mucous and saliva. The advantage of having a plurality of inlets 20 is that if one inlet 20 is blocked, the remaining inlets 20 can still admit gas. Furthermore, all of the inlets 20 must be blocked in order to overcome the resistance of inlets 20 to entry by solids, liquids or their mixtures thereof, since the force applied at the gas analyzer tends to cause an increased negative pressure differential between the pressure within air collector 18, and the pressure external to air collector 18, if inlets 20 are all blocked. This increased negative pressure differential permits solids, liquids, or their mixtures thereof, to enter inlets 20. As soon as one inlet 20 is no longer blocked, for example by the intake of material contained within inlet 20, the negative pressure differential is reduced to its former levels, and inlets 20 can again resist entry by solids, liquids or their mixtures thereof. Thus, only minimal amounts of material can enter at one time.

The preferred embodiment illustrated in FIGS. 1–3, 5 and 7 has maximum resistance to blockade by, or intake of, solids, liquids or their mixtures thereof. This preferred embodiment has three substantially tubular inlets 20, or three substantially flush inlets 24, placed symmetrically with respect to each other. Such a configuration maximizes the distance between inlets 20 or 24, thereby rendering inlets 20 or 24 less likely to be blocked by a single particle of solids, or a single droplet of liquids, or their mixtures thereof, such as mucous or saliva. Requiring more than one such particle or droplet for blockage decreases the likelihood of all three inlets 20 or 24 being blocked simultaneously, and thus reduces the likelihood of intake of solids, liquids, or their mixtures thereof. The distance from inlets 20 or 24 to the inner wall of tube 12 is also maximized, so that inlets 20 or 24 are preferably placed close to the center of tube 12, where the airstream has the maximum flow rate, providing a faster response time. Such a configuration further decreases the likelihood of particles or droplets of solids, liquids, or their mixtures thereof, becoming trapped between inlets 20 or 24 and the inner wall of tube 12.

The substantially tubular shape of inlets 20 provides an even greater advantage over inlets 24, since the projection of inlets 20 away from the surface of air collector 18 denies physical support to particles or droplets of solids, liquids or their mixtures thereof, increasing the likelihood that these particles or droplets break up and are moved away by the flow of the gas. Furthermore, the curved shape of spherical air collector 18 in the preferred embodiment, as shown in FIGS. 1, 2, 4 and 7, also enhances the resistance to blockade, since solids, liquids or their mixtures thereof, tend to slide off air collector 18, rather than depositing on air collector 18. The formation of such deposits, as is seen in the air adaptors known in the literature described above, increases the need for maintenance and decreases the lifespan of air adaptors. Thus, the ability of air collector 18 of the present invention to resist such deposits increases the working lifespan of air adaptor 10.

In addition to achieving a superior performance in gas sampling, air adaptor 10 of the present invention has a second method of use: the administration of medicines in a nebulized or otherwise airborne pharmaceutical preparation to the patient via port 14 of the present invention. In this method, such medicines are placed within port 14. When the patient inhales, the medicine is pulled from port 14, through air collector 18 and into tube 12. From tube 12, the medicine is pulled into the endotracheal tube of the patient, and from there into the patient's lungs.

TESTING OF THE MULTIPLE CHANNEL SAMPLE PORT

The features and embodiments illustrated herein may be better understood with reference to the experiments described below. These experiments were conducted on air adaptors according to the present invention, as well as on examples of air adaptors which employ a number of well-known systems for separating gases from liquids, solids, or their mixtures thereof.

Experimental Methods

All tests were performed at room temperature (22°–27° C.). The term "T-5 piece" refers to an air adaptor with a substantially straight tube. All tests employed a standard T-piece for comparisons, defined as "Standard T-piece" under *Experimental Materials* below, with the exception of the Response Time Test, which used a specially designed T-piece for comparisons.

1. Microdrops Test—A nebulizer was placed 135 mm from the T-piece to be tested. Air flow through the nebulizer was 5.0 L/min. Water was nebulized in the nebulizer and sucked towards the T-piece by means of the volume ventilator. The volume ventilator (LP-6) had the following parameters: $V=0.8$ L; $BR=14$ min$^{-1}$. The flow through the line from the tube of the T-piece was 47 ml/min. Water which passed from the nebulizer, through the T-piece and into the line was captured in a water trap and measured. This method for capturing and measuring water was used in all subsequent experiments.

2. Macrodrops Test—A tube was placed 8–10 mm from the T-piece to be tested. Macrodrops of water and egg white flowed from the tube at a rate of 18 ml/min, and were sucked towards the T-piece by means of the volume ventilator (LP-6), which had the following parameters: $V=1.6$ L; $BR=14$ min$^{-1}$.

3. Humid Air Test—Moisture was added to air to a relative humidity of 95–100%. The humid air flowed into the T-piece by means of the volume ventilator, which had the following parameters: $V=0.8$ L; $BR=14$ min$^{-1}$. The flow of gas in the line was 47 ml/min. The temperature was 30°–32° C. inside the ventilation system and the T-piece.

4. Air Flow Resistance at T-piece Intake—The T-piece to be tested was placed between two additional standard T-pieces. Air flow through this three T-piece system was established at 30 L/min. Pressure drop for this flow was measured with and without the tested T-piece. The difference represented the resistance.

5. Air Flow Resistance at T-piece Outflow—A second standard T-piece was connected to the outlet of the T-piece to be tested. The first end of the second T-piece was connected to a differential pressure meter. The second end was connected to an air pump. The air flow was 50 ml/min. The pressure drop was measured by means of the differential pressure meter.

6. Response Time Test—The response time was measured, using a method defined by regulation prEN864 for capnography. The T-piece used for comparisons was specially designed to have minimal hindrances to a rapid response, such that the response time of this fast response time T-piece was minimal. After the response time of the fast response time T-piece was measured, the fast response time T-piece was exchanged for the T-piece to be tested, and the response time of the T-piece to be tested was measured. The difference between the response time of the fast response time T-piece and the response time of the T-piece to be tested was calculated.

Experimental Materials

T-pieces were constructed from the following materials, and were tested according to the above methods. Results are given in Table 1 below, in the form of comparisons to the standard T-piece.

1. Standard—A standard T-piece was used as a reference for all of these experiments. This standard T-piece had a port with a single, very large, inlet, which was found to be the most effective of the previously known airway adaptor designs. This inlet was located in the center of the tube, which is the most effective location for the inlet to a sample port. The large size of the inlet had the advantage of resisting both blockage by solids, liquids, or their mixtures thereof. The large size also promoted resistance towards the intake of small particles or droplets of solids, liquids, or their mixtures thereof, since the flow rate was very slow at this inlet. Unfortunately, the slow flow rate also caused a slow response time.

2. Hollow Fiber, Flat Membrane, Cylinder—Filters, formed from hydrophobic porous media, were constructed in the form of hollow fibers, flat porous membranes, or porous cylinders, and were inserted into the port of the T-piece. The resistance at outflow is the initial resistance measured, and is therefore the lowest resistance offered by these T-pieces, since the resistance generated by hydrophobic filters tends to increase over time. Also, the response time of the hollow fibers is an estimate.

3. Walls/Nets—Protective netting barriers, flow directing plates, drop-shaped bodies were inserted into the port of the T-piece; or, T-pieces were made with a wave shape or with a bend in the form of a "Z". These systems had the disadvantage of being larger than standard T-pieces.

4. Water Traps—Water traps were constructed from water absorptive materials, or by altering the internal geometry of the T-piece. These systems had the disadvantage of being larger than standard T-pieces, and of becoming very heavy after water trapping.

5. Minimal Input—The diameter of the port of the T-piece was reduced to 0.8 mm internal diameter.

6. Maximal Input—The diameter of the port of the T-piece was increased to 2.5 to 4 mm internal diameter.

7. Air Collector with 3 Substantially Tubular Inlets—The airway adaptor of the present invention was tested both in its most preferred embodiment as shown in FIGS. 1 and 2, with a substantially spherical air collector, and in a second embodiment as shown in FIG. 5, with a substantially oval-shaped air collector. In both embodiments, the air collector had three substantially tubular inlets. The airway adaptor of the present invention had a great improvement in performance over other T-pieces. The airway adaptor of the present invention had a 4–5 times improvement in performance on the microdrops test, as compared to the standard T-piece. Furthermore, no water entered the port of the airway adaptor of the present invention at all during the macrodrops test, while the standard T-piece admitted 4 ml/hour. The resistance at air intake was a pressure drop of no more than 0.1 mBar, under a 30 L/min flow rate. The resistance at air outflow was negligible: a pressure drop of about 0.2–0.3 mBar under a flow rate of 50 ml/min. The response time improved by about 70%, as compared to the standard T-piece, and was very close to that of the T-piece with minimal input. In fact, the response time of the airway adaptor of the present invention is as minimal as is possible for T-piece constructions.

TABLE 1

Results of Tests of T-pieces

| | T-piece Type | Microdrops Test | Macrodrops Test | Humid Air Test | Resistance at Intake for 30 L/min Flow | Resistance at Outflow for 30 L/min Flow | Response Time (msec) |
|---|---|---|---|---|---|---|---|
| | | (ml H$_2$O intake/hour) | | | (pressure drop, mBar) | | |
| | Standard | 0.90 | 4.0 | 0.055–0.70 | 0.1 | <0.1 | 91 |
| Hydrophobic Porous Media | Hollow Fiber | Blockage after several hours | — | — | — | 10–20 | >90–100 |
| | Flat Membrane | Blockage after several hours | — | — | — | 2–4 (at start) | 110–120 |
| | Cylinder | Water penetration after several hours | — | — | — | 2–3 | 60–62 |
| | Walls/ Nets | Poor water protection | | — | <0.1 | — | — |
| | Water Traps and Baffles | — | — | Limited life span | — | — | — |
| | Minimal Input | 0 | 1.6 | 0.047 | <0.1 | 0.2 | 48–53 |
| | Maximal Input | 0.30 | 0.70 | 0.065 | — | <0.1 | 60–65 |
| | Air Collector with 3 Substantially Tubular Inlets | 0.20–0.35 | No water intake | 0.05 | 0.1 | 0.2 | 52–56 |

While the invention has been described with respect to a limited number of embodiments, it will be appreciated that many variations, modifications and other applications of the invention may be made.

What is claimed is:

1. An airway adaptor, comprising:
   (a) a tube, said tube featuring a wall; and
   (b) a port forming a junction with said tube through said wall, said port including an outlet, an air collector and a plurality of inlets, said air collector being attached to said outlet, and said inlets being attached to said air collector, each of said inlets featuring an opening, and said opening being located substantially within said tube.

2. The airway adaptor of claim 1, wherein said inlets are holes.

3. The airway adaptor of claim 2, wherein the internal diameter of each of said holes is substantially similar to said internal diameter of each of said other holes.

4. The airway adaptor of claim 3, wherein said internal diameter lies in a range of from about 0.5 mm to about 1.7 mm.

5. The airway adaptor of claim 4, wherein said internal diameter is about 0.8 mm.

6. The airway adaptor of claim 1, wherein said inlets are substantially tubular.

7. The airway adaptor of claim 6, wherein said inlets and said air collector are formed of substantially hydrophobic material.

8. The airway adaptor of claim 6, wherein said air collector is formed of substantially hydrophilic material, and said inlets are formed of substantially hydrophobic material.

9. The airway adaptor of claim 6, wherein each of said inlets has a substantially similar internal diameter and a substantially similar length as each of said other inlets, and each of said openings has a substantially similar internal diameter as each of said other openings.

10. The airway adaptor of claim 9, wherein said internal diameter of each of said inlets and of each of said openings lies in the range of from about 0.5 mm to about 1.7 mm.

11. The airway adaptor of claim 10, wherein said internal diameter of each of said inlets and of each of said openings is about 0.8 mm, and said length of each of said inlets is about 2.5 mm.

12. The airway adaptor of claim 6, wherein said inlets project into said air collector, such that an end of each of said inlets is located substantially within said air collector, and there is a first distance between each of said ends, and a second distance between each of said openings, said first distance being less than said second distance.

13. The airway adaptor of claim 1, wherein said openings of said inlets are substantially facing one end of said tube.

14. The airway adaptor of claim 13, wherein said plurality of inlets is three inlets, and each of said inlets is symmetrically disposed relative to each other of said inlets.

15. The airway adaptor of claim 1, wherein said opening of at least one of said inlets is substantially facing one end of said tube, and said opening of at least another one of said inlets is substantially facing the other end of said tube.

16. The airway adaptor of claim 1, wherein said air collector is substantially centrally located within said tube, and said air collector is substantially perpendicular to said wall of said tube.

17. The airway adaptor of claim 1, wherein said air collector is a hollow sphere.

18. The airway adaptor of claim 17, wherein the external diameter of said air collector is less than about 5.5 mm.

19. The airway adaptor of claim 1, wherein said outlet has a first internal diameter, and each of said openings of said inlets has a second internal diameter, said first internal diameter being greater than said second internal diameter.

20. A method of using the airway adaptor of claim 1 for withdrawing a sidestream, comprising:
   (a) attaching the airway adaptor to a conduit for conducting gas;
   (b) connecting said outlet of said port to a gas analyzer; and
   (c) applying a force at said gas analyzer, such that gas flowing through the airway adaptor moves from the airway adaptor to said gas analyzer.

21. A method of using the airway adaptor of claim 1 for administering medicine, comprising:
   (a) connecting said airway adaptor to a breathing apparatus of a patient; and
   (b) placing the medicine in said port of the airway adaptor.

* * * * *